(12) United States Patent
Saso et al.

(10) Patent No.: US 8,475,821 B2
(45) Date of Patent: Jul. 2, 2013

(54) BONE PROSTHETIC MATERIAL AND METHOD OF MANUFACTURING THE SAME

(75) Inventors: Takamasa Saso, Tokyo (JP); Ryuichi Mizutani, Tokyo (JP)

(73) Assignee: Brain Base Corporation, Tokyo (JP)

( * ) Notice: Subject to any disclaimer, the term of this patent is extended or adjusted under 35 U.S.C. 154(b) by 172 days.

(21) Appl. No.: 12/996,303

(22) PCT Filed: Jun. 5, 2009

(86) PCT No.: PCT/JP2009/060308
§ 371 (c)(1),
(2), (4) Date: Dec. 3, 2010

(87) PCT Pub. No.: WO2009/148147
PCT Pub. Date: Dec. 10, 2009

(65) Prior Publication Data
US 2011/0097373 A1    Apr. 28, 2011

(30) Foreign Application Priority Data

Jun. 5, 2008  (JP) .................................. 2008-147655

(51) Int. Cl.
| | |
|---|---|
| *A61F 2/28* | (2006.01) |
| *A61K 33/42* | (2006.01) |
| *A61K 33/06* | (2006.01) |
| *C04B 35/64* | (2006.01) |

(52) U.S. Cl.
USPC ........... 424/422; 424/423; 424/602; 424/682; 264/653

(58) Field of Classification Search
None
See application file for complete search history.

(56) References Cited

U.S. PATENT DOCUMENTS 6,358,532 B2 *  3/2002  Starling et al. ................ 424/489
2002/0165616 A1  11/2002  Heide et al.
(Continued)

FOREIGN PATENT DOCUMENTS

| CN | 1686576 A | 10/2005 |
|---|---|---|
| CN | 101146557 A | 3/2008 |

(Continued)

OTHER PUBLICATIONS

Office Action issued in corresponding Chinese Patent Application No. 200980120807.6 on Dec. 31, 2013.

(Continued)

*Primary Examiner* — Ernst Arnold
(74) *Attorney, Agent, or Firm* — Sughrue Mion, PLLC

(57) ABSTRACT

A method of manufacturing a bone prosthetic material, includes by forming tricalcium phosphate (TCP) particle precursor particles; by performing preliminary sintering on the TCP precursor particles at a temperature in a first temperature range to produce TCP particles of diameters in a predetermined diameter range; by granulating the TCP particles to produce granulated bodies; and by performing sintering on the granulated bodies at a temperature in a second temperature range to generate sinter assemblies. The second temperature range is higher than the first temperature range. In the bone prosthetic material manufactured thus, a first space in a range of 100 to 400 µm is formed between adjacent two of a plurality of sintered assemblies. Each of the plurality of sintered assemblies includes tricalcium phosphate (TCP) particles which are subjected to sintering, and a second space in a range of 5 to 100 µm is formed between adjacent two of the TCP particles. The second space communicates with the first space. Each of the plurality of sintered assemblies has a connection portion connecting the TCP particles, and the connection portion has a width in a range of 5 to 20 µm.

13 Claims, 8 Drawing Sheets

U.S. PATENT DOCUMENTS

2005/0098915 A1* 5/2005 Long et al. .................. 264/109
2007/0218098 A1 9/2007 Reif et al.
2008/0026057 A1* 1/2008 Benke ........................ 424/468

FOREIGN PATENT DOCUMENTS

| JP | 05-237178 A | 9/1993 |
| JP | 11-322458 A | 11/1999 |
| JP | 2005-052224 A | 3/2005 |
| JP | 2006-122606 A | 5/2006 |
| JP | 2006-320442 A | 11/2006 |
| JP | 2008-035981 A | 2/2008 |
| JP | 2008-086676 A | 4/2008 |
| WO | 2008/087798 A1 | 7/2008 |

OTHER PUBLICATIONS

Extended Search Report issued in corresponding European Patent Application No. 09758414.8 on Apr. 8, 2013.

Database EPI/Thompson, Week 200856 (Sep. 3, 2008), "Manufacture Method Live Body Tissue Prosthesis Material Forming Mix Pre Sinter Calcium Phosphate Powder Bind Particle Sphere Shape", Thomson Scientific, London, GB.

* cited by examiner

BONE PROSTHETIC MATERIAL AND METHOD OF MANUFACTURING THE SAME

TECHNICAL FIELD

The present invention relates to a bone prosthetic material for which bone can be predictably regenerated in a short time in a defect portion of a jawbone and other bones, and a method of manufacturing the same.

BACKGROUND ART

In these years, in a case of treating a tooth affected by a periodontal disease, an endosseous dental implant method has been employed in which the affected tooth is extracted and then an artificial tooth root is embedded into the extracted portion of a jawbone. In this case, since a part of the jawbone is affected by the periodontal disease, so that the jawbone part is lost, the artificial tooth root could not be supported sufficiently. For this reason, in order to regenerate the lost portion of the jawbone, various methods have been considered.

As one of the methods, a calcium phosphate based bone prosthetic material in a granular or block shape is used. However, since a dense sintered body and dense phosphate glass (bioglass) are used as the bone prosthetic materials in this method, these materials are hard to be absorbed into a living body. For this reason, a long time period is required to completely replace the bone prosthetic material with an autologous bone.

In addition, there are many kinds of calcium phosphate such as hydroxyapatite (HAP) and tricalcium phosphate (TCP). Because the hydroxyapatite (HAP) of them has biocompatibility but is hard to be absorbed into a living body, there is a possibility that the hydroxyapatite remains in the body after treatment for a long time period. Meanwhile, since tricalcium phosphate (TCP) has bioresorbable, it does not remain in the body after the treatment by being displaced by new bone tissue and accordingly can be easily handled. In addition, there are two kinds of tricalcium phosphate of $\alpha$-tricalcium phosphate ($\alpha$-TCP) and $\beta$-tricalcium phosphate ($\beta$-TCP), and since having higher bioresobability than that of $\beta$-TCP, $\alpha$-TCP is absorbed into the living body more quickly.

When granular material formed of $\alpha$-TCP or $\beta$-TCP is embedded into a bone defect portion, the granular material is absorbed by osteoclastic cells and simultaneously a bone tissue is regenerated around the granular material by osteoblast cells. In this manner, the granular material is gradually replaced with the autologous bone. As described above, $\alpha$-TCP and $\beta$-TCP are replaced with the bone tissue by cells. However, it is desirable that $\alpha$-TCP and $\beta$-TCP are gradually absorbed in association with generation of a new bone without being absorbed immediately. When having a short replacement time period, $\alpha$-TCP is absorbed before the bone tissue is sufficiently generated, and accordingly there is a possibility that $\alpha$-TCP cannot serve as a scaffold of the generation of bone. In addition, the replacement reaction occurs on a surface of the granular material contacting cells, and accordingly a surface structure and an extent of a surface area in the granular material will be important factors.

As shown in JP 2006-122606A, the inventors of the present application focused attention on characteristics of $\alpha$-TCP or $\beta$-TCP, and proposed a bone prosthetic material whose inner portion is formed of $\beta$-TCP and whose surface portion is formed of $\alpha$-TCP, in order to reduce a regeneration period as much as possible.

Additionally, as a technique focusing on a role of the granular material, JP-A-Heisei 5-237178 proposes a bone prosthetic material formed of calcium phosphate based ceramics having a dense portion and a porous portion. In this bone prosthetic material, a cellular porous portion is produced by use of foaming agent mixed into this material. It is not described how the osteoblast cells enter the porous portion, and also is not clarified how the existence of the porous portion influences the regeneration period of bone.

As described above, a technique for treating and regenerating a defected bone in a short time is not yet proposed actually.

From this reason, a regeneration mechanism of bone has been studied and analyzed, and a knowledge described below has been found. Specifically, existence of osteoblast cells is required in the regeneration of bone, and blood is essential to keep the existence of the osteoblast cells. The knowledge shows that if the bone prosthetic material fills a bone defect portion, and the osteoblast cells and the blood can be sufficiently supplied to a surface of the bone prosthetic material (by a blood capillary and an arteriole vessel), the regeneration of bone can be realized in a short time.

CITATION LIST

[Patent Literature 1]: JP 2006-122606A
[Patent Literature 2]: JP-A-Heisei 5-237178

SUMMARY OF THE INVENTION

On the basis of the above-described knowledge, the present invention provides a bone prosthetic material that makes it possible to regenerate a bone in a short time, and a method of manufacturing the same.

In an aspect of the present invention, a manufacturing method of the bone prosthetic material includes producing tricalcium phosphate (TCP) particle precursor particles; preliminarily sintering the TCP particle precursor particles at a temperature in a first temperature range to produce TCP particles having a diameter in a predetermined range; granulating the TCP particles to produce granulated bodies; and sintering the granulated bodies at a temperature within a second temperature range to produce sintered assemblies. The second temperature range is higher than the first temperature range.

In another aspect of the present invention, a bone prosthetic material includes a plurality of sintered assemblies, and a first space of 100 to 400 µm is formed between adjacent two of the sintered assemblies. Each of the plurality of sintered assemblies is formed from tricalcium phosphate (TCP) particles. A second space of 5 to 100 µm is formed between the TCP particles, and the second space communicates with the first space. The TCP particle has the size of 25 to 75 µm. In addition, the sintered assembly includes a connection portion having the width of 5 to 25 µm to couple the TCP particles to each other. In addition, the connection portion is formed in a process of sintering in the second temperature range.

According to the present invention, the sintering is carried out so that the spherical tricalcium phosphate (TCP) particles can be coupled via the connection portion. In this manner, the bone prosthetic material has a sufficient strength, and has a surface area increased by the space formed between the TCP particles. Since a blood capillary enters and comes out the space of the bone prosthetic material, osteoblast cells attach to the increased surface, and accordingly bone can be regenerated in a short time. In addition, since the spherical particles are coupled to each other via the connection portion to form the sintered assembly, an arteriole vessel can enter the space formed between the sintered assemblies when the sintered assemblies are adjoined. In this manner, the regeneration efficiency of the bone can be improved. Furthermore, since the sintered assembly filled in a bone defect portion serves as a spacer of the bone defect portion, a soft tissue to inhibit the regeneration of new bone is prevented from entering the bone defect portion. In addition, since the particles having a diameter less than 25 μm are removed by classifying the preliminarily sintered spherical particles, a foreign-body reaction due to the particle cannot occur. Moreover, unlike the conventional example, since a cellular porous portion is not formed by using forming agent, the bone prosthetic material and a manufacturing method of the same are simplified.

DESCRIPTION OF EMBODIMENTS

Hereinafter, a bone prosthetic material and a manufacturing method of the same according to the present invention will be described below with reference to attached drawings.

In order to regenerate a bone absorbed and lost due to a lesion and the like, the bone prosthetic material according to the present invention is filled in a defect portion. For this purpose, the bone prosthetic material comprises tricalcium phosphate (TCP) having high biocompatibility and bioresorbability as a main component. In addition to the tricalcium phosphate (TCP), the bone prosthetic material may include hydroxyapatite (HAP). The bone prosthetic material is filled into the defect portion, serves as a spacer of the defect portion, and thus suppresses approach of a soft tissue. In addition, a new bone is regenerated from a surface of the filled prosthetic material. Moreover, the prosthetic material is gradually absorbed into a living body, and finally the bone prosthetic material is completely replaced with the new bone. The reaction occurs when osteoblast cells attach to a surface of the prosthetic material. Therefore, it is desirable that the bone prosthetic material is formed of a material having high biocompatibility and bioresorbability. In addition, a structure of the bone prosthetic material is important. Especially, when the bone prosthetic material is filled as the spacer of the defect portion, it is advantageous to shorten a regeneration period that a surface area of the prosthetic material is large.

Figure 2:
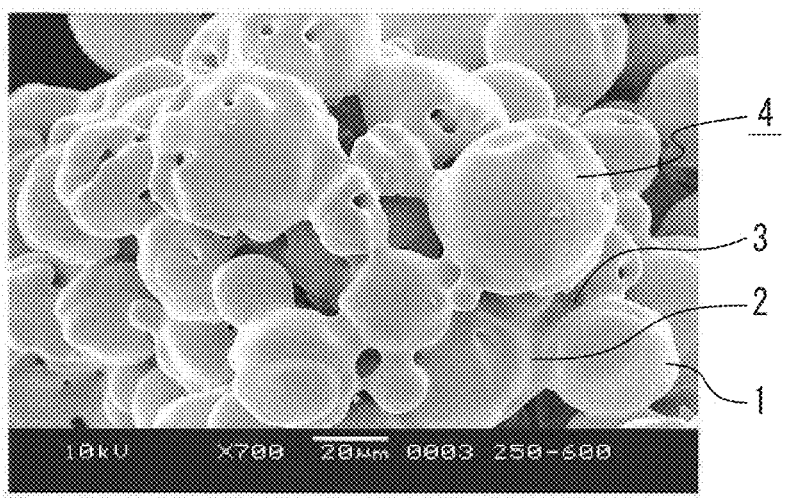
FIG. 2 is an SEM image of a sintered assembly when particles are α-TCP (700-power imaging magnification)
Figure 3:
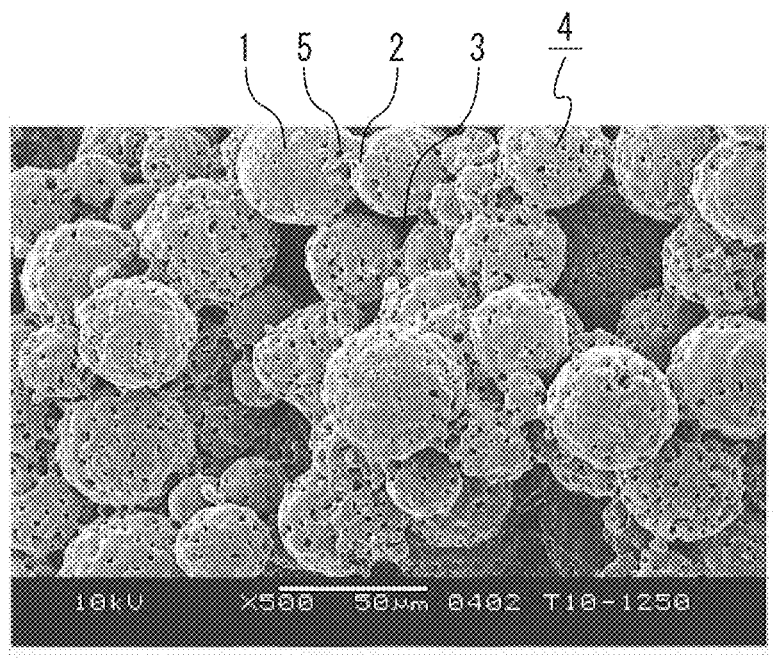
FIG. 3 is an SEM image of the sintered assembly when the particles are β-TCP (500-power imaging magnification)

As shown in FIGS. 2 and 3, the bone prosthetic material serving as the spacer has spherical TCP particles 1 with a size in a range of 25 to 75 μm, and the spherical TCP particles are coupled by connection portions having the width in a range of 5 to 20 μm and a length in a range of 5 to 10 μm. Thus, a space 3 is formed between the spherical TCP particles. These values were measured from a scanning electron microscope (SEM) photograph. Other dimensions were measured in the same manner. The space has a size in a range of 5 to 100 μm, and communicates with an outside. Accordingly, the osteoblast cells, blood capillaries having a diameter of approximately 10 μm, and the like can enter the space. The spherical TCP particles 1 are coupled to each other via the connection portions as described above, and have a sufficiently-sustainable strength as the prosthetic material.

It should be noted that the connection portion is formed through material-movement of a part of components of the respective TCP particles to the connection portion between the TCP particles, and thus is formed of the same components as those of the TCP particle. In addition, a material-movement amount of the material-movement varies depending on a preliminary sintering temperature. In the sintering, the connection portion grows greatly and buries the space between the TCP particles in case of the TCP particles of the range of 25 to 75 μm in the preliminary sintering temperature less than 1000° C. Additionally, in the preliminary sintering temperature of 1300° C. or more, the connection portion cannot be formed sufficiently in the sintering.

Moreover, the spherical TCP particles are formed to have sizes in the range of 25 to 75 μm. However, the spherical TCP particles have some unevenness on the surface and sometimes are distorted, and accordingly this value shows a totally-averaged diameter of the TCP particle.

In addition, the sintered assemblies having sizes in a range of approximately 150 to 2000 μm can be collected by classifying sintered assemblies produced by granulating the spherical TCP particles into granular bodies and sintering the granular bodies. Accordingly, when the sintered assemblies are collected, spaces in a range of approximately 100 to 400 μm have been formed between the adjoining sintered assemblies. An arteriole vessel enters this space, and the osteoblast cells can attach.

It should be noted the sintered assemblies are formed to have the sizes in the range of 150 to 2000 μm. However, the sintered assemblies have some unevenness on the surface and sometimes are distorted, and accordingly this value shows a totally-averaged diameter of the sintered assembly.

As tricalcium phosphate (TCP) material, α-TCP and β-TCP are employed. Here, α-TCP has higher biocompatibility than that of β-TCP. Accordingly, considering the regeneration period, α-TCP only, β-TCP only, or mixture of α-TCP and β-TCP is arbitrarily selected and used. In addition, in formation of the spherical TCP particles, hydroxyapatite (HAP) having high bioresorbability is sometimes mixed to TCP by 5 to 35%. In this case, an action to induce the osteoclastic cells due to negative charge on a surface of hydroxyapatite can be expected.

As described below, the spherical TCP particle 1 is formed to be in a dense state or in a state having a pore 5 in a range of 1 to 5 μm, depending on a condition such as the preliminary sintering temperature (FIG. 2 and FIG. 3). As described above, when the pore 5 is formed in the spherical TCP particle 1, the osteoblast cells and the like further easily attach to the pore 5.

Figure 7:
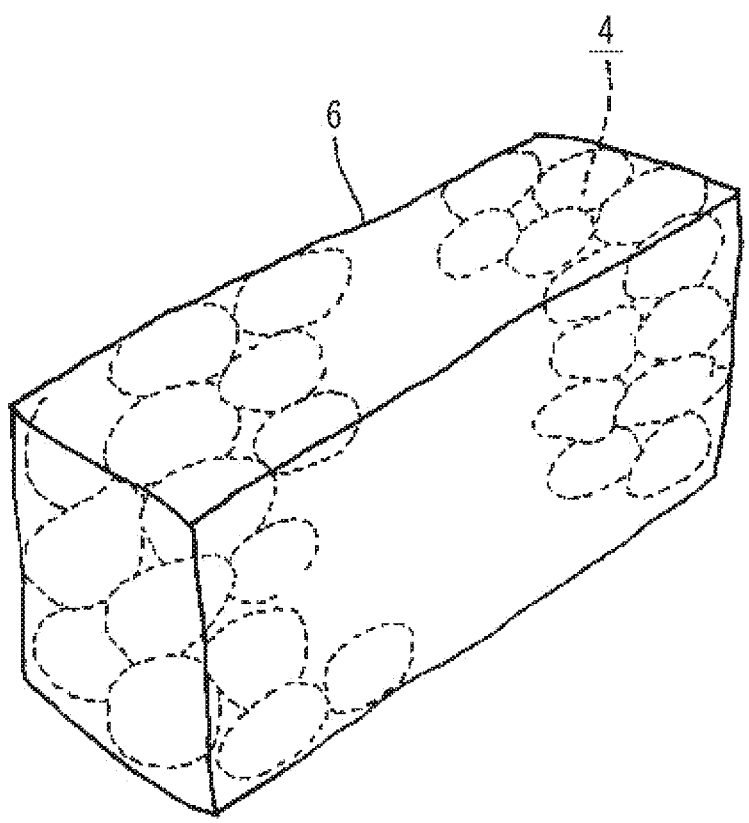
FIG. 7 is a perspective view showing when the sintered assemblies are stored in a bag.
Figure 8:
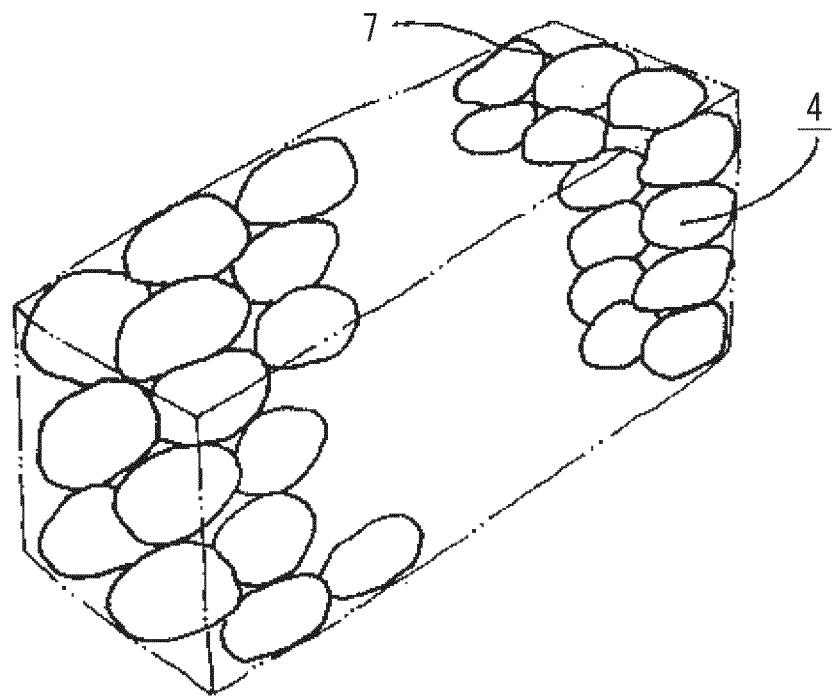
FIG. 8 is a perspective view showing when the sintered assemblies are bonded in a block with an adhesive agent.

The sintered assembly 4 of the spherical TCP particles (FIG. 1) may be directly filled into a defect portion (a bone regeneration portion), and the sintered assemblies are stuffed in a bag 6 having bioresorbability and biocompatibility, so that the bag is inserted into the defect portion (a bone regeneration portion) (FIG. 7). It should be noted that Gelatin or collagen is used as a material of the bag. In addition, the sintered assemblies 4 may be bonded with an adhesive agent 7 having adequate bioresorbability to be formed in a plate shape or in a block so as to be adaptive for a shape of the bone regeneration portion (FIG. 8).

Figure 9:
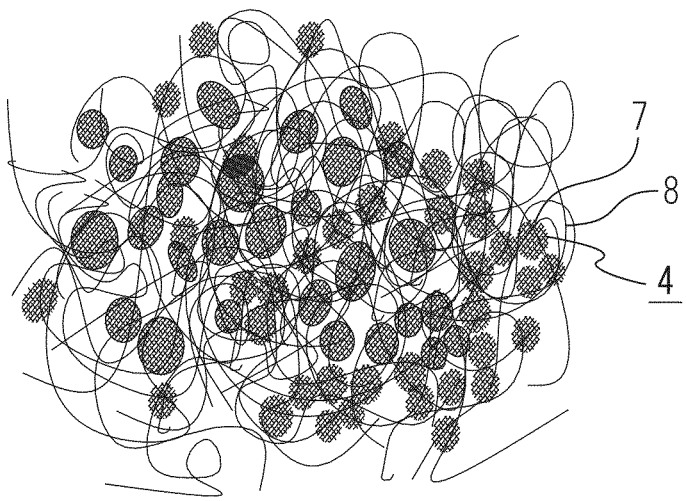
FIG. 9 is a perspective view showing when the sintered assemblies are adhered to fibers.

Moreover, the plurality of sintered assemblies 4 may be adhered by a paste agent having bioresorbability, and the plurality of sintered assemblies 4 may be attached to a non-woven fibers 8 having adequate bioresorbability with the adhesive agent 7 (FIG. 9), may be entwined in the nonwoven fibers 8, or may be inserted and retained between cloth-shaped two-layered fibers 8. It should be noted that as a material of the above-mentioned fibers, a polylactide material or collagen is employed.

The manufacturing of the spherical TCP particles is carried out in a process described below. Precipitation product particles are obtained by using highly-purified calcium hydroxide solution and phosphate solution as raw materials and by neutralizing these solutions. The precipitation product particles are suspended in pure water. Subsequently, by drying the suspended solution in a spray-dry method, spherical particles having diameters in a predetermined range are produced as the TCP particle precursor particles. Subsequently, the TCP particle precursor particles are preliminarily sintered at 1050° C., and then, by classifying the sintered particles by using a screen to remove the sintered particles with the diameters less than 25 μm, the TCP particles 1 with the diameters of in a range of 25 to 75 μm are obtained. Then, by granulating the TCP particles, granulated bodies with diameters in a range of 150 to 2000 μm are obtained. In this granulating, the granulating is carried out at a main axis rotation frequency of 300 rpm and at the granulating axis rotation frequency of 3000 rpm in a granulator, delivering drops of 10% aqueous solution of hydroxypropylcellulose (HCP-L) as binder. The granulated bodies are sintered at a temperature of 1250° C. for 5 hours. However, the sintering time is not limited to 5 hours. In this manner, the bone prosthetic material including the monophase sintered assembly 4 of α-TCP is obtained. In the sintered assembly, the spherical granulated bodies are jointed to each other by the connection portions generated in the sintering process.

In addition, two kinds of spherical TCP particle precursor particles which are synthesized by using the ultra-purified calcium hydroxide including Mg elements less than 100 ppm as raw material, and precursor particles which are obtained by adding Mg elements up to 100 to 1000 ppm so as to form solid solution in which TCP is replaced with Mg elements, in order to extend a stable temperature range of β-phase TCP to 1300° C., are subjected to preliminarily sintering separately to produce the spherical TCP particles 1. The TCP particles with the diameters of less than 25 μm are removed by classifying by use of the screen. The two kinds of spherical TCP particles are mixed and granulated, and the granulated bodies are sintered at 1250° C. for 5 hours. Thus, the bone prosthetic material formed from the sintered assemblies of TCP particles including both of α phase and β phase is produced.

As described above, when the β-TCP monophase bone prosthetic material is manufactured, it is desirable that the sintering temperature for the sintered assembly 4 is set to a temperature of 1000° C. to 1135° C. However, in order to intend to give a further strength to the sintered assembly, the granulated bodies to which Mg elements are added up to 100 to 10000 ppm are sintered at 1200° C. to 1300° C.

As the preliminary sintering temperature for the above-mentioned spherical TCP particles, 1000° C. to 1200° C. is adequate. A TCP particles formed from densely-firmed spherical particles are produced by sintering at a temperature less than 1000° C., so that the space of 5 to 100 μm is not formed between the particles. Accordingly, the space allowing the entering of the blood capillary and the osteoblast cells cannot be formed.

When the preliminary sintering temperature is set to 1000° C. or more and less than 1125° C., a pore 5 in a range of 1 to 5 μm is formed in the spherical particle itself, and also the bone prosthetic material having the space 3 can be obtained. Moreover, when the preliminary sintering temperature is set to 1125° C. to 1200° C., the spherical particles become dense, and also the bone prosthetic material having the above-mentioned space can be obtained.

As the sintering temperature of the above-mentioned granulated bodies, 1150° C. to 1430° C. higher than the temperature of the preliminary sintering is adequate. In any case, it is desirable to be higher than the above-mentioned preliminary sintering temperature.

It should be noted that in a case of the preliminary sintering at 1200° C. or more and less than 1300° C., the strength of the sintered assembly is not sufficient, and accordingly, the sintering temperature after the granulation is required to be set to 1300° C. to 1430° C.

Manufacturing Example 1

The precipitation particles are synthesized by using ultra-purified calcium hydroxide solution containing Mg less than 12 ppm as raw material, are suspended in pure water to be in 11% of solid content, and then are dried by a spray dry method to produce TCP particle precursor particles. The dried TCP particle precursor particles are subjected to preliminarily sintering at 1200° C. for 2 hours. Thus, the spherical TCP particles 1 are obtained.

The obtained spherical TCP particles are classified with a screen to remove the particles with the diameters less than 25 μm, and the granulating is carried out at a main axis rotation frequency of 300 rpm and at the granulating axis rotation frequency of 3000 rpm of in a granulator. Thus, granulated bodies with the diameters of 150 to 2000 μm are obtained. At this time, 10% solution of hydroxypropylcellulose (HPC-L) was dropped to the particles as binder so as to be 4% to the granulated bodies.

Figure 1:
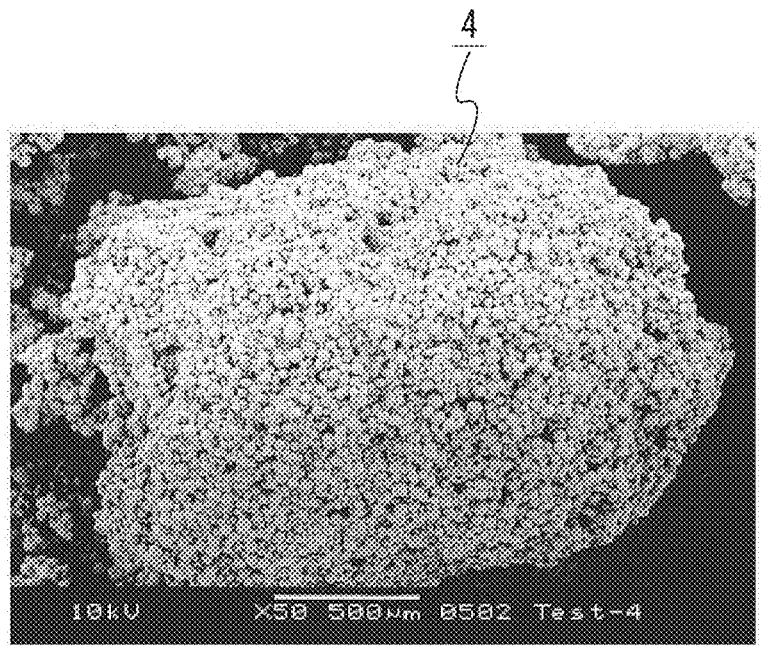
FIG. 1 is an SEM (Scanning Electron Microscope) image of a block of granulated bodies in a manufacturing process of a bone prosthetic material according to one embodiment of the present invention (20-power imaging magnification)
Figure 4:
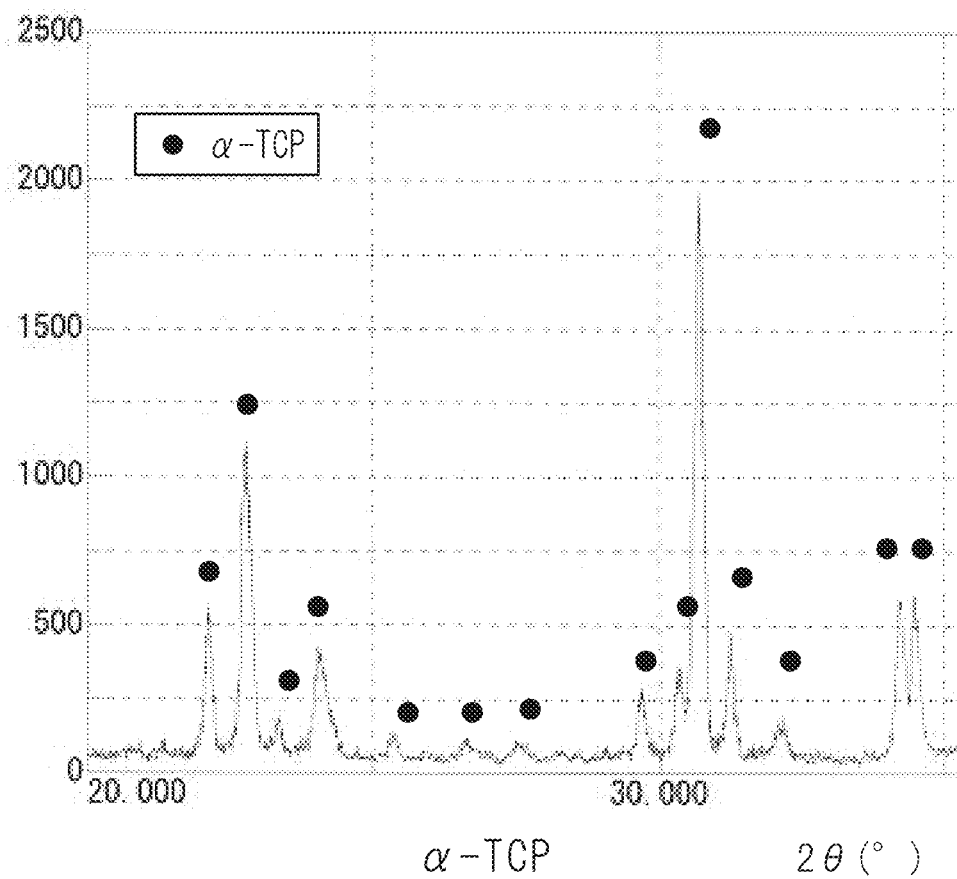
FIG. 4 is an X-ray diffraction profile of the sintered assembly of FIG. 2.

After drying the above-mentioned granulated bodies at 105° C., the granulated bodies are sintered at 1300° C. for 5 hours so that the sintered assemblies are obtained such that the spherical TCP particles are coupled to each other by the connection portions 2 to form the spaces 3 having the sizes in the range of 5 to 100 μm between the spherical TCP particles. The bone prosthetic material is obtained by classifying the sintered assemblies with a screen and selecting the sintered assemblies 4 in the range of 150 to 2000 μm (FIG. 1). Examining the sintered assemblies 3 by an X-ray diffraction, the sintered assemblies are in the α-TCP monophase (FIG. 4).

Manufacturing Example 2

Figure 5:
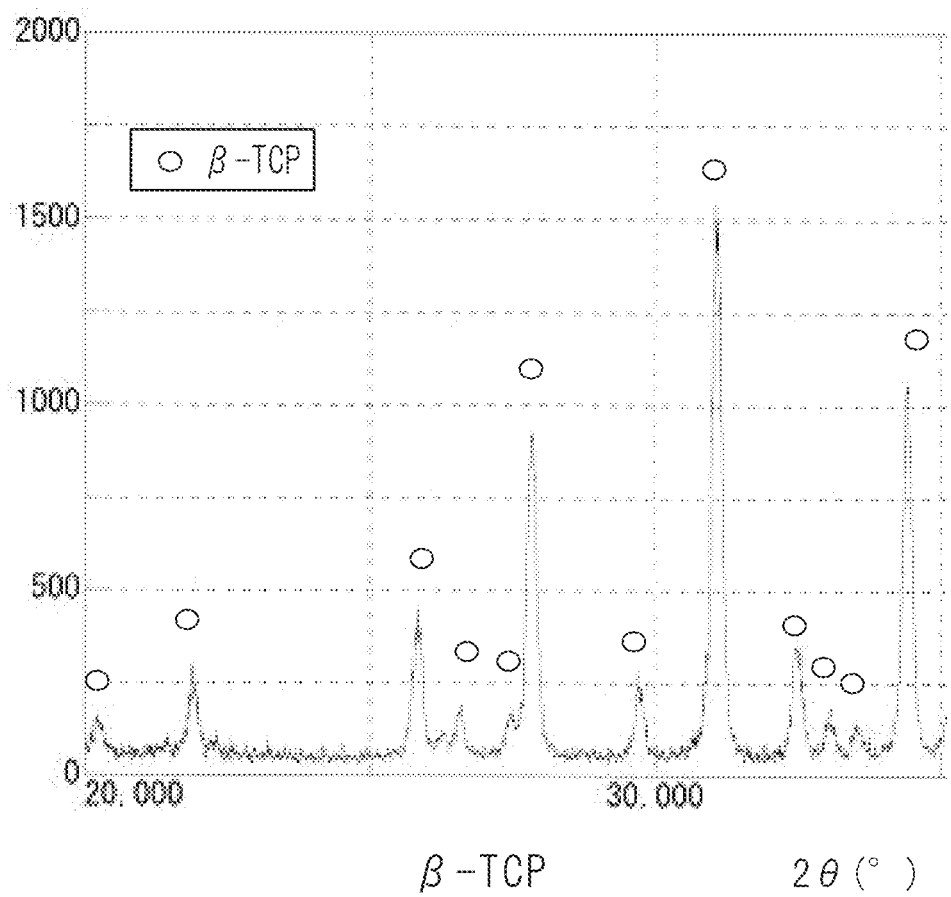
FIG. 5 is an X-ray diffraction profile of the sintered assembly of FIG. 3.

The precipitation suspending solution in which the solid content obtained in the manufacturing example 1 is 11% is dried with a spray dry method to produce the spherical TCP particle precursor particles. Then, preliminarily sintering is performed to the TCP particle precursor particles at 1050° C.

for 2 hours to produce TCP particles. The spherical TCP particles 1 with the diameters in a range of 25 to 75 μm are obtained by classifying the obtained TCP particles with a screen to remove the particles with the diameters less than 25 μm. The obtained spherical TCP particles are granulated by the granulator in the manufacturing example 1 by adding 10% solution of hydroxypropylcellulose (HPC-L) as binder so as to be 5.5% of solid content. After drying the granulated bodies at 105° C., the granulated bodies are sintered at 1135° C. for 5 hours, and thus the bone prosthetic material formed of the sintered assemblies is obtained (FIG. 3). Examining the sintered assembly in the X-ray diffraction, the sintered assembly was in the β-TCP monophase (FIG. 5). In this manner, the spaces 3 in a range of 5 to 100 μm are formed between the spherical TCP particles. It should be noted that the pore 5 was formed in the above-mentioned spherical TCP particle.

Manufacturing Example 3

The granulated bodies are sintered at 1250° C. for 5 hours, and thus the bone prosthetic material of α-TCP monophase was obtained. In this manner, the spaces in the range of 5 to 100 μm are formed between the spherical TCP particles.

Manufacturing Example 4

Pure water suspended solution in which the precipitation in which a content amount of Mg is prepared to be 6400 ppm in order to extend the stable temperature range of the β phase to be 1250° C. or more, is prepared to be at 11% of solid content is dried by a spray dry method to obtain TCP particle precursor particles. Then, the TCP particle precursor particles are subjected to preliminarily sintering at 1200° C. for 2 hours so that the spherical TCP particles are obtained. The TCP particles with diameters in a range of 25 to 75 μm are obtained by classifying the obtained TCP particles with a screen to remove particles of less than 25 micrometers.

The obtained spherical TCP particles in the range of 25 to 75 μm and the spherical TCP particles obtained in the manufacturing example 1 are mixed and then the mixed particles are granulated at the main axis rotation frequency of 300 rpm and at the granulating axis rotation frequency of 3000 rpm in the granulator. Thus, the granulated bodies in a range of 150 to 2000 μm are obtained. At this time, 10% solution of hydroxypropylcellulose (HPC-L) was dropped to the granulated particles as binder so as to be 4% to the granulated particles.

Figure 6:
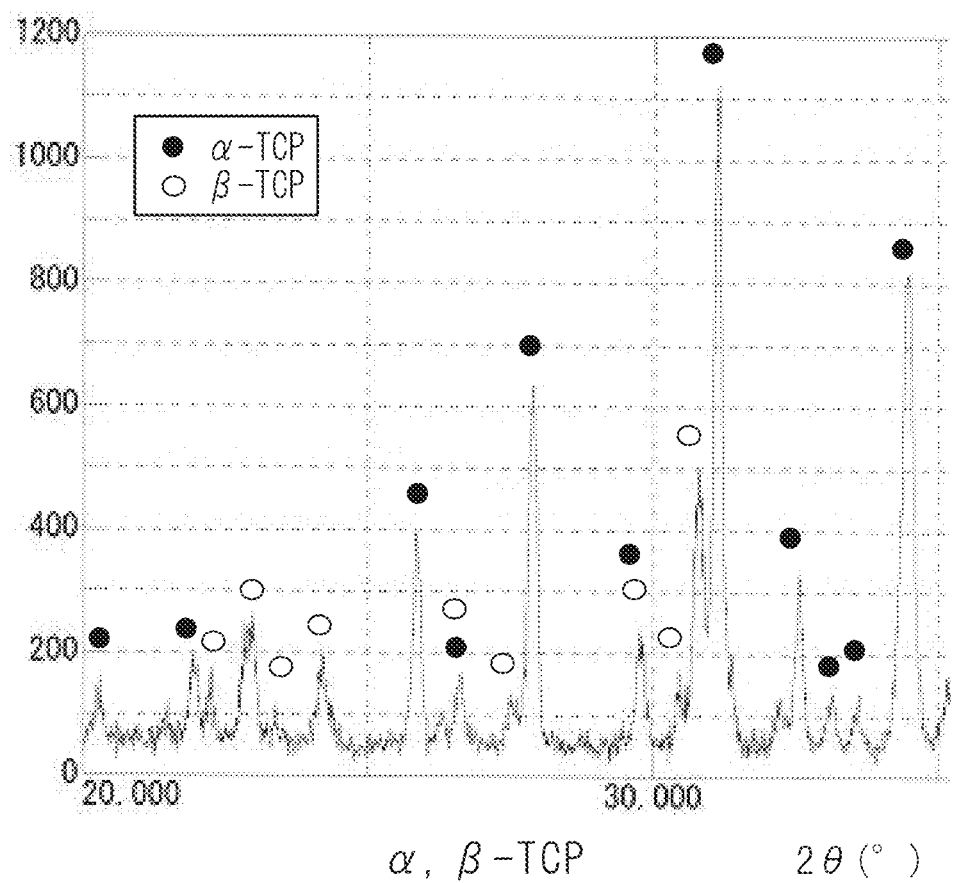
FIG. 6 is an X-ray diffraction profile of the sintered assembly when the particles are α-TCP and β-TCP.

After drying the granulated bodies at 105° C., the granulated bodies are sintered at 1250° C. for 5 hours, and thus the bone prosthetic material with both of α-phase and β-phase mixed was obtained (FIG. 6). In this manner, the spaces in a range of 5 to 100 μm are formed between the spherical TCP particles.

Manufacturing Example 5

Figure 10:
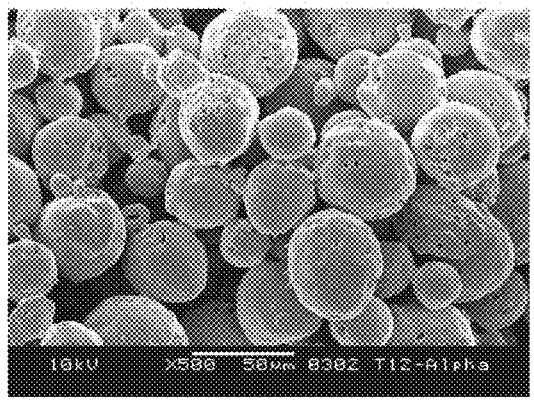
FIG. 10 shows an example of a sintered assembly obtained in a manufacturing example 5.

FIG. 10 shows an example of the sintered assemblies obtained when the preliminary sintering is carried out at 1310° C. for 2 hours in the manufacturing example 1, and then, the sintering is carried out at 1400° C. for 5 hours after the classification and the like. From FIG. 10, it could be understood that the connection portions are not adequately formed.

Manufacturing Example 6

Figure 11:
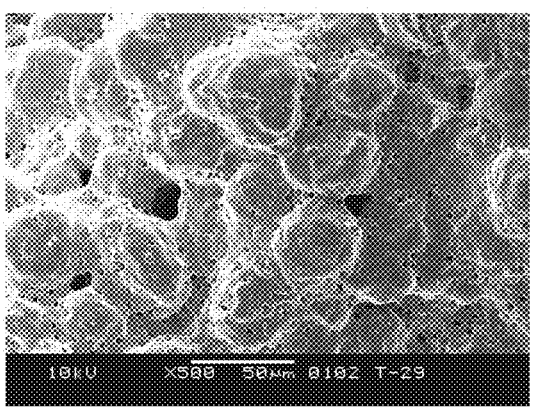
FIG. 11 shows an example of a sintered assembly obtained in a manufacturing example 6.

FIG. 11 shows an example of the sintered assemblies obtained when the preliminary sintering is carried out at 975° C. for 2 hours in the manufacturing example 1, and then, the sintering is carried out at 1250° C. for 5 hours after the classification and the like. From FIG. 11, the connection portions grow too much and bury the spaces between the TCP particles.

Manufacturing example 7

Figure 12:
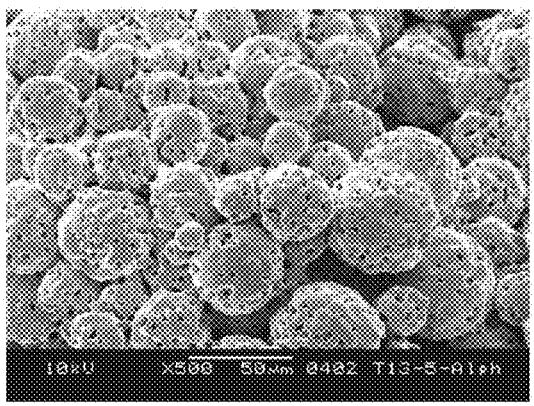
FIG. 12 shows an example of a sintered assembly obtained in a manufacturing example 7.

FIG. 12 shows an example of the sintered assemblies obtained when the preliminary sintering is carried out at 1010° C. for 2 hours in the manufacturing example 1, and then, the sintering is carried out at 1250° C. for 5 hours after the classification and the like. The connection portions in the range of 5 to 20 μm are formed, the pore 5 is further formed on the surface of the TCP particle, and accordingly desired characteristics for the bone prosthetic material are provided.

As seen from the above-mentioned manufacturing examples, the connection portion is formed in the sintering. In this case, the shape of the connection portion and the state of the pore 5 on the surface of the TCP particle vary depending on the preliminary sintering temperature.

When the preliminary sintering temperature is less than 1000° C., the connection portion grows too much and bury the space between the particles. Accordingly, the space in the range of 5 to 100 μm desired as the bone prosthetic material cannot be obtained.

Meanwhile, when the preliminary sintering temperature exceeds 1300° C., the connection portion is not sufficiently formed.

In addition, when the preliminary sintering temperature exceeds 1100° C., the pore 5 is not formed on the surface of the TCP particle. When the preliminary sintering temperature is in a range of 1000° C. to 1100° C., the pore 5 is formed.

As described above, the preliminary sintering temperature is desired to be 1000° C. or more and 1300° C. or less.

As described above, various examples have been described. However, the present invention is not limited to the above-mentioned examples. Various modifications can be realized within the scope of the present invention, and the modifications are also included in the present invention.

The invention claimed is:

1. A method of manufacturing a bone prosthetic material, comprising:
    forming tricalcium phosphate (TCP) particle precursor particles;
    performing preliminary sintering on said TCP particle precursor particles at a temperature of between 1000° C. and 1300° C., so as to provide TCP particles with diameters in a range of 25 μm to 75 μm;
    granulating said TCP particles to produce granulated bodies with diameters in a range of 150 μm to 2000 μm; and
    performing sintering on said granulated bodies at a temperature of between 1135° C. and 1430° C., to produce a bone prosthetic material comprising a plurality of sintered assemblies,
    wherein in said sintered assemblies, the spacing between adjacent TCP particles is between 5 μm and 100 μm,
    and wherein in said bone prosthetic material, the spacing between adjacent sintered assemblies is between 100 μm and 400 μm.

2. The method according to claim 1, wherein said preliminary sintering further comprises the step of removing TCP particles having diameters of less than 25 μm.

3. The method according to claim 1, wherein said forming TCP particle precursor particles comprises:
    adding Mg elements to said TCP particle precursor particles.

4. The method according to claim 1, wherein the granulating of said TCP particles comprises:
   granulating said TCP particles in the presence of hydroxypropylcellulose as a binder, to produce said granulated bodies.

5. A bone prosthetic material comprising a plurality of sintered assemblies, wherein the sintered assemblies comprise tricalcium phosphate (TCP) particles that have been subjected to preliminary sintering and which have diameters in a range of 25 μm to 75 μm,
   wherein the sintered assemblies have been subjected to sintering and have diameters in a range of 150 μm to 2000 μm,
   wherein in said sintered assemblies, the spacing between adjacent TCP particles is between 5 μm and 100 μm,
   wherein in said bone prosthetic material, the spacing between adjacent sintered assemblies is between 100 μm and 400 μm,
   and wherein in said bone prosthetic material, the spaces between adjacent sintered assemblies interconnect with the spaces between adjacent TCP particles.

6. The bone prosthetic material according to claim 5, wherein the sintered assemblies each have a connection portion formed between adjacent TCP particles, and said connection portion having a width of between 5 μm and 20 μm.

7. The bone prosthetic material according to claim 5, wherein said TCP particles have a pore of between 1 μm and 5 μm.

8. The bone prosthetic material according to claim 5, wherein said TCP particles are selected from the group consisting of α-TCP particles, β-TCP particles, or a mixture of α-TCP particles and β-TCP particles.

9. The bone prosthetic material according to claim 5, wherein said sintering assemblies further comprise hydroxyapatite (HAP).

10. The bone prosthetic material according to claim 5, wherein said sintering assemblies are stored in a bag which has bioresorbablity.

11. The bone prosthetic material according to claim 5, wherein said sintering assemblies are joined in a plate or a block.

12. The bone prosthetic material according to claim 5, wherein said sintering assemblies are joined with a paste material.

13. The bone prosthetic material according to claim 5, wherein said sintering assemblies are attached to fibers having bioresorbability.

* * * * *